United States Patent [19]
Pezeshkian

[11] Patent Number: 5,636,986
[45] Date of Patent: Jun. 10, 1997

[54] DRILL GUIDE FOR DENTAL IMPLANTS AND METHOD

[76] Inventor: Alex A. Pezeshkian, 1831 Deer Mont Rd., Glendale, Calif. 91207

[21] Appl. No.: 597,108

[22] Filed: Feb. 6, 1996

[51] Int. Cl.$^6$ .............................. A61C 3/00; A61C 3/02; A61C 11/00
[52] U.S. Cl. ...................... 433/76; 433/213; 433/75
[58] Field of Search ...................... 433/75, 72, 76, 433/213

[56] References Cited

U.S. PATENT DOCUMENTS

| | | | |
|---|---|---|---|
| 1,380,040 | 5/1921 | Chayes | 433/76 |
| 3,407,503 | 10/1968 | Nealon | 433/76 |
| 5,055,042 | 10/1991 | Jansen | 433/76 |
| 5,320,529 | 6/1994 | Pompa | 433/76 |

FOREIGN PATENT DOCUMENTS

| | | | |
|---|---|---|---|
| 512181 | 8/1939 | United Kingdom | 433/76 |

Primary Examiner—Cary E. O'Connor
Attorney, Agent, or Firm—Gerald L. Price

[57] ABSTRACT

A drill guide system for use in the installation of dental implants. The guides are configured in the shape of teeth and have drill bushings passing through to guide and position the drill so that the resulting hole will receive an implant that is properly positioned and aligned. The guides are provided in different configurations depending on the number of adjacent implants to be installed and have a depending pin to position the guide in an initial drilled hole. By being configured in the shape of teeth, the dental surgeon is able to position the guide prior to drilling and be able to observe how the resulting work will appear once the actual prosthetics are installed on the implants. The drill bushings not only guide the drill but provide additional patient security since the possibility of slippage or breakage of the drill bit during drilling is substantially reduced.

5 Claims, 1 Drawing Sheet

DRILL GUIDE FOR DENTAL IMPLANTS AND METHOD

BACKGROUND OF THE INVENTION

The present invention relates generally to dental implant surgery and more particularly to a new and improved drill guide system for positioning the drill during implant surgery.

Dental implants are regarded as one of the fastest growing specialty in dentistry and the dollar volume of procedure billing has experienced a compounded annual growth rate of 44%. over the last ten years. Dental implants are devices that are designed to be screwed into the human jawbone and serve as a mounting for a prosthetic in the shape and color of the tooth it is replacing. The primary advantage of implants over bridgework and partial dentures is that the installation is of a permanent nature and does not require the care, maintenance, comfort problems or adjustment associated with bridgework and dentures.

The implant device itself is generally cylindrical in nature with a lower portion having a standard or self tapping screw configuration and an upper portion defining a post with a mount for attaching an implant prosthetic. The implant is installed in the course of a surgical procedure wherein a properly positioned hole is drilled into the jawbone at the location of the missing tooth and the implant is screwed into the hole by means of tapped threads or a self tapping implant. After installation the jawbone will grow and tighten its grip on the implant and thereafter a prosthetic that is shaped and colored to conform to the original tooth is attached to the implant post by means of a cooperative mounting between the top of the implant and the prosthetic.

It will be readily appreciated that to achieve proper alignment and appearance, the location and angle of the hole that the dental surgeon drills to receive the implant is very important. In many cases the hole has been drilled on a trial and error basis starting with an undersized drill and correcting the angle and position with the final drill. Such a procedure is very time consuming and still fails to ensure proper final alignment and appearance. There have been several drilling guides on the market but in general they fail to provide a complete and cost effective solution since they fail to fully position the drill for a single drilling operation, some have to be made up for each patient which is not cost effective and they all fail to properly guide the drill during the drilling operation.

SUMMARY OF THE INVENTION

It is the general aim of the present invention to provide a new and improved drilling guide for the installation of dental implants that ensures proper location, alignment and is can be used repeatedly, yet which also provides additional protection and safety during the drilling process by providing drill bushings to prevent slippage or error during the drilling procedure.

It is another object of the invention to provide an implant drilling guide that can be readily used with different number of tooth locations and which also provides the dental surgeon with an indication of how the installed prosthetic will appear.

BRIEF DESCRIPTION OF THE DRAWING

Additional objects and advantages of the invention will appear from the following description taken in conjunction with the accompanying drawings in which.

Figure 1:
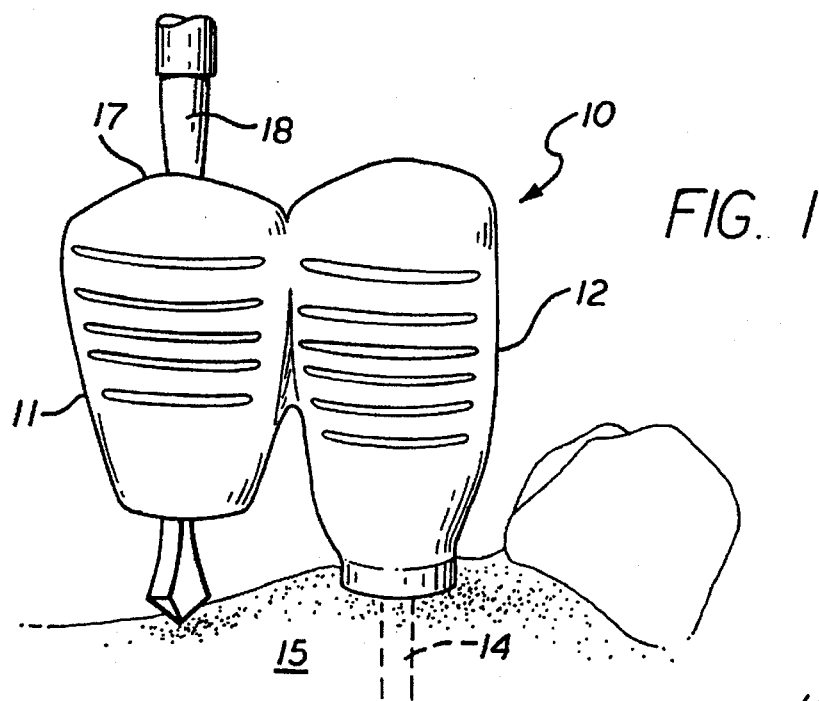
FIG. 1 is a perspective view of an exemplary drill guide embodying the features of the present invention.

While the present invention is susceptible of various modifications and alternative constructions, illustrative embodiments are shown in the drawings and will herein be described in detail. It should be understood however, that it is not to be intended to limit the invention to the particular forms disclosed, but, on the contrary, the intention is to cover all modifications, equivalents, and alternative construction falling within the spirit and scope of the invention as expressed in the appended claims.

DESCRIPTION OF THE PREFERRED EMBODIMENT

Referring now to FIG. 1, an exemplary implant drilling guide generally indicated at 10 is illustrated in the form of a guide for installing two adjacent implants, the guide including two housings 11 and 12 that are fixed together in a size and configuration to resemble adjacent teeth. The housing 12 is provided with a pin 14 shown here in dotted lines, which is sized to be firmly inserted in a hole that has been drilled in the jaw bone 15 to receive same.

In accordance with one of the important aspects of the present invention, provision is made for drilling holes for implant installation that are properly spaced and aligned. This is accomplished by providing housing 11 with a generally vertically disposed drill guide or bushing 17 that is sized to receive a drill 18 of the size used for implant installation which is usually 2 or 3 millimeters in diameter. A drill bushing is preferred over a drill guide hole since it is made of a hardened metal and further serves to prevent the drill from slipping or bending and breaking during drilling.

In use, the pin 14 is inserted into an initial hole that has been drilled into the jawbone. The entire drill guide fixture can then be rotated about the axis of the pin until the two tooth shaped shells are positioned properly. At this point, the dental surgeon can drill the hole for the adjacent implant and thereafter remove the fixture 10 and install the implants in the two holes.

Figure 2:
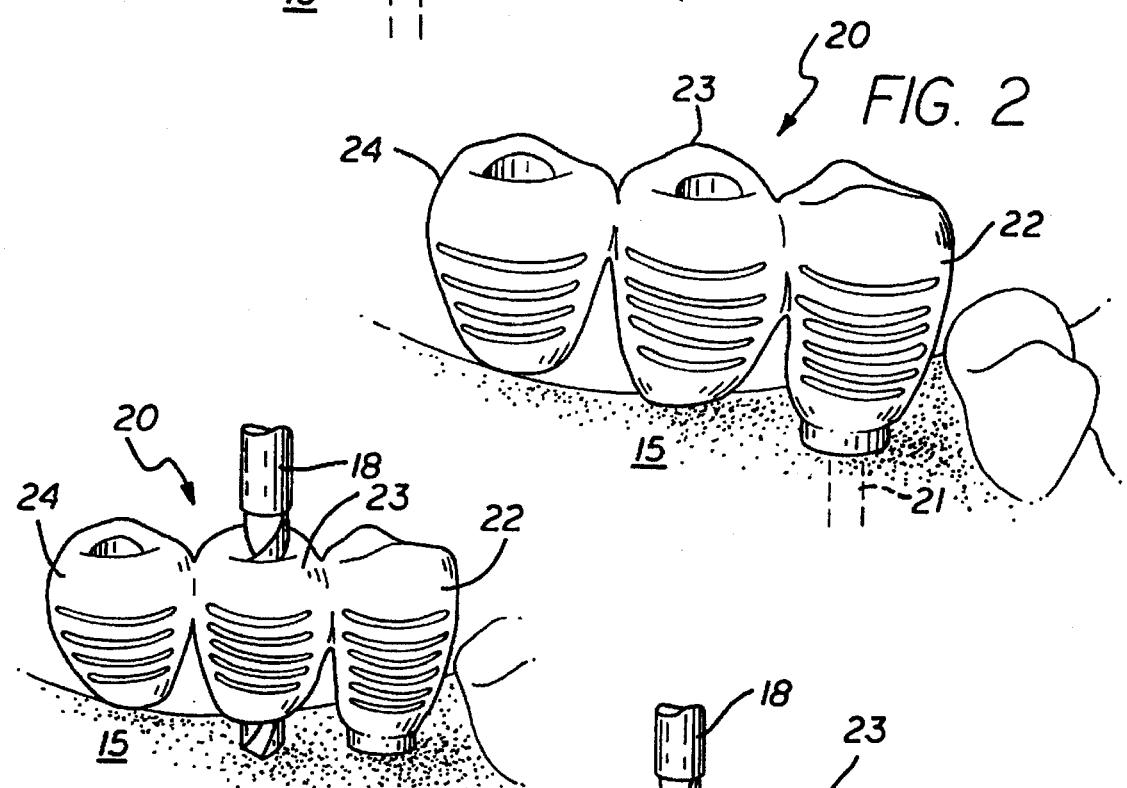
FIG. 2 is a perspective view of an exemplary drill guide for use in the installation of three adjacent implants.
Figure 3:
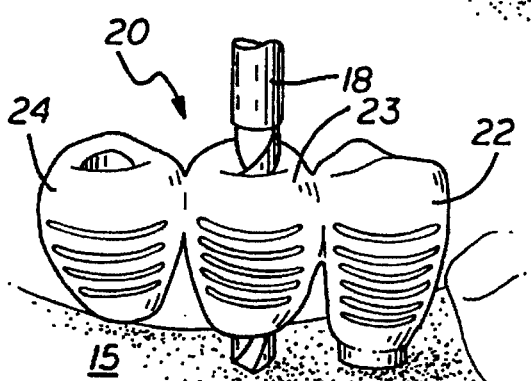
FIG. 3 is the view shown in FIG. 2 with the middle implant hole being drilled.
Figure 4:
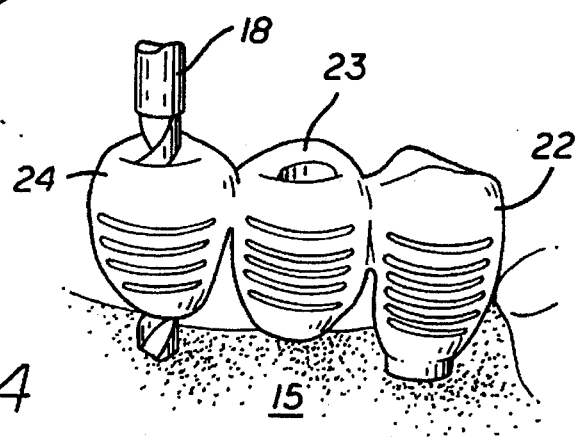
FIG. 4 is the view shown in FIG. 2 with the end implant hole being drilled.

Referring collectively to FIGS. 2 through 4, a guide 20 conforming to the present invention is depicted in a configuration for use in installing three adjacent implants. The use of this guide in a surgical procedure would be essentially the same as the two tooth guide 10. An initial hole is drilled into the jawbone to position the guide 20 by means of a pin 21 that depends from housing 22. The pin 21 is inserted into said hole and the entire fixture is then rotated about the axis of pin 21 until the three tooth shaped housings 22, 23 and 24 are properly aligned. The holes for the two adjacent implants can then be drilled as shown in FIG. 3 and FIG. 4. The fixture 20 can then be removed and the implants can then be installed in the three holes.

The initial hole which is utilized for a single implant and also for providing the initial locating hole for multiple implant guides such as 10 and 20 is located by means of an individually fabricated surgical guide stent. This procedure is well known by dental practitioners. A distance of 3.5 mm from the initial hole to the adjacent tooth is recommended to prevent prosthetic problems.

What I claim is:

1. A guide for drilling holes for installing dental implants comprising at least two connected housings with at least one sized and configured as a tooth, at least one pin depending from one of said housings whereby upon insertion of said pin into a hole drilled into the jawbone, said housings will be located in a manner corresponding to the location of prosthetic teeth and means on at least one housing for guiding a drill in a predetermined path.

2. The guide set forth in claim 1 wherein said means for guiding a drill comprises a generally vertical hole through said housing and sized to receive and guide a drill for drilling into a jawbone.

3. The guide set forth in claim 2 wherein said generally vertical hole further comprises a drill bushing.

4. The guide set forth in claim 1 wherein said pin is removably attached to said housing.

5. The method of drilling holes into a jawbone to receive a plurality of dental implants comprising the steps of locating and drilling an initial hole, inserting a pin into said initial hole which depends from a housing shaped and sized as a tooth with at least one additional housing affixed thereto which is also shaped and sized as a tooth with a drill guide passing therethrough, aligning said additional housing to conform to the position of an actual tooth by rotating the housing about said pin until said additional housing is properly positioned and inserting a drill into said drill guide and drilling into the jawbone to receive an implant.

* * * * *